(12) United States Patent
Wiedmann

(10) Patent No.: US 8,092,220 B2
(45) Date of Patent: Jan. 10, 2012

(54) METHOD FOR RECONSTRUCTION OF TEETH

(76) Inventor: Manfred Wiedmann, Steinheim (DE)

( * ) Notice: Subject to any disclaimer, the term of this patent is extended or adjusted under 35 U.S.C. 154(b) by 265 days.

(21) Appl. No.: 12/519,332

(22) PCT Filed: Dec. 14, 2007

(86) PCT No.: PCT/EP2007/010988
§ 371 (c)(1),
(2), (4) Date: Jul. 2, 2009

(87) PCT Pub. No.: WO2008/077508
PCT Pub. Date: Jul. 3, 2008

(65) Prior Publication Data
US 2010/0009317 A1    Jan. 14, 2010

(30) Foreign Application Priority Data
Dec. 21, 2006   (DE) .................. 10 2006 060 682

(51) Int. Cl.
*A61C 13/08* (2006.01)
(52) U.S. Cl. .................................. 433/202.1
(58) Field of Classification Search ............. 433/201.1, 433/202.1
See application file for complete search history.

(56) References Cited

U.S. PATENT DOCUMENTS

| | | | |
|---|---|---|---|
| 1,378,527 A | 5/1921 | Dalbey | |
| 1,378,745 A | 5/1921 | Wavrin | |
| 1,469,893 A | 10/1923 | Clapp | |
| 2,535,163 A * | 12/1950 | Scott | 33/513 |
| 2,752,689 A * | 7/1956 | Adams et al. | 33/513 |
| 3,049,804 A | 8/1962 | Skinner | |
| 4,528,627 A * | 7/1985 | Coben | 433/68 |
| 4,611,288 A | 9/1986 | Duret et al. | |
| 4,718,850 A * | 1/1988 | Knebelman | 433/72 |
| 5,278,756 A * | 1/1994 | Lemchen et al. | 600/587 |
| 5,482,048 A * | 1/1996 | Johnson | 600/476 |
| 5,639,235 A | 6/1997 | Lapointe et al. | |
| 5,659,625 A * | 8/1997 | Marquardt | 382/118 |
| 5,951,498 A * | 9/1999 | Arnett | 600/587 |
| 6,261,248 B1 * | 7/2001 | Takaishi et al. | 600/590 |
| 7,128,572 B2 * | 10/2006 | Lauciello et al. | 433/26 |

(Continued)

FOREIGN PATENT DOCUMENTS

AT    32656    3/1988

(Continued)

OTHER PUBLICATIONS

Hasanreisoglu, U. et al., An analysis of maxillary anterior teeth: facial and dental proportions, J Prosthet Dent., vol. 94, No. 6, pp. 530-538, Dec. 2005.*

(Continued)

*Primary Examiner* — John P Leubecker
*Assistant Examiner* — Christopher Sponheimer
(74) *Attorney, Agent, or Firm* — Daniels Patent Law PLLC; Scott A. Daniels

(57) ABSTRACT

A method for the reconstruction of missing, broken and/or abraded teeth by means of face analysis. In order to determine the shapes and sizes of the teeth, the face of a patient, for whom the teeth are intended, is measured by means of one or more image-type pictures. The respective tooth size and tooth shape is determined proportionally from the obtained values.

10 Claims, 4 Drawing Sheets

U.S. PATENT DOCUMENTS

| | | | |
|---|---|---|---|
| 7,699,607 B2 * | 4/2010 | Margossian | 433/73 |
| 7,833,013 B2 * | 11/2010 | Diers et al. | 433/72 |
| 2008/0090207 A1 * | 4/2008 | Rubbert | 433/171 |

FOREIGN PATENT DOCUMENTS

| | | |
|---|---|---|
| CA | 2100009 | 7/1993 |
| EP | 0091876 | 10/1983 |
| EP | 1563804 | 12/2004 |
| FR | 2525103 | 4/1982 |

OTHER PUBLICATIONS

Frederick, K., Maxillary incisor crown form and crowding in adolescent orthodontic patients, The University of Tennessee Health Science Center, May 2008.*

* cited by examiner ns of the lower end of the nose and the nasal wing the second incisor, and the profile of the cheek the canine tooth.

The inventor has also discovered that the respective side of a patient which is more strongly set-up can be identified from the face, along with the fact resulting from this that the dentures are in general more harmonic on the side which is more strongly set-up, whereas the teeth are less regular on the side which is less strongly set-up.

Therefore, according to the invention, the distance of the bipupil line to the corner of the mouth line is determined in order to reconstruct the side of the patient which is more strongly set-up, the side with a greater length being stipulated to be the harmonic side.

Taking this fact into account makes it possible to match the false teeth or dentures even more closely to the original teeth or original set of teeth.

METHOD FOR RECONSTRUCTION OF TEETH

FIELD OF THE INVENTION

The invention relates to a method for reconstructing missing, broken and/or abraded teeth.

BACKGROUND OF THE INVENTION

Replacing natural teeth by producing false teeth from the originals of natural teeth and their use in dentures does not constitute a problem under normal circumstances.

However, the reconstruction of missing, broken and/or abraded teeth, that is to say of teeth for which the original tooth is no longer available or no longer completely available, is problematic. If no photo of the patient with a photo of the face existed "perchance", in which, e.g. as a result of a smile, the teeth were visible, false teeth could with respect to their shape and size only be used on the basis of estimations and the available space in the mouth.

This also resulted in the risk of changing the appearance of the patient, in particular if a number of teeth of the upper jaw or even the entire upper jaw had to be replaced.

The present invention is therefore based on the object of providing a method by means of which replacement teeth can be produced even in the case of missing, broken and/or abraded teeth, which replacement teeth correspond as far as possible to the natural teeth in their shape and size.

SUMMARY OF THE INVENTION

According to the invention, this object is achieved by a method in which a reconstruction of missing, broken and/or abraded teeth is carried out by means of facial analysis, the face of a patient, for whom the teeth are provided, being measured by means of one or more image records in order to determine the shapes and sizes of the teeth, whereupon the respective tooth size and tooth shape is determined in proportion from the obtained values.

The inventor has discovered from lengthy and complex series of trials that shapes and sizes of teeth can be derived from certain features, shapes and dimensions of the face of the patient. This also holds when the teeth of the patient are already missing or are (partially) destroyed. This insight was used systematically by the inventor for reconstructing natural teeth. To this end, an image record, e.g. a photographic image, of the face of the patient was taken in the form of a frontal image. The face of the patient was measured on the basis of the produced photo, whereupon the obtained values subsequently allowed deduction of the corresponding proportion of the teeth sizes and teeth shapes.

A very advantageous method which approximates reality very closely can consist of determining the original width of the nasal base for reconstructing the spacing of the tips of the two canine teeth of the patient from one another, the determined value being provided as a corresponding proportion for determining the widths of the other teeth in proportional form.

This insight then makes it possible to determine the respective widths of the six most important teeth of dentures, namely the two front teeth, the two lateral incisors and the two canine teeth, in accordance with the original teeth.

The shapes and sizes of all other teeth can then be determined from further features of the face; for example, the contour of the face can produce the central front tooth, the ratio of the widths of the nasal base and nasal root, the diago-

BRIEF DESCRIPTION OF THE DRAWINGS

Advantageous developments and refinements result from the dependent claims and from the exemplary embodiment described in principle below on the basis of the drawing, in which:

DETAILED DESCRIPTION OF THE INVENTION

For reasons of simplicity and for improved clarity, the face of the patient in the figures is illustrated in the form of a line illustration. In practice, an image of the patient with a closed mouth is produced in this context for reconstructing the teeth. The image can be effected arbitrarily, for example in digital form, as a result of which it is possible to illustrate different refinements and reconstructions of the teeth in connection with the photographic image. Likewise, image processing and transfer to a computer are possible in this manner. This makes it possible for the measures for measuring the face of the patient for tooth reconstruction, carried out subsequently, to also be carried out using a computer program with corresponding software.

The following exemplary embodiment describes the reconstruction of the two front teeth 1, the two incisors 2 and the two canine teeth 3 of the upper jaw. In general, a reconstruction of the teeth of the upper jaw which is as true as possible is important for the facial shape of the patient.

Figure 1:
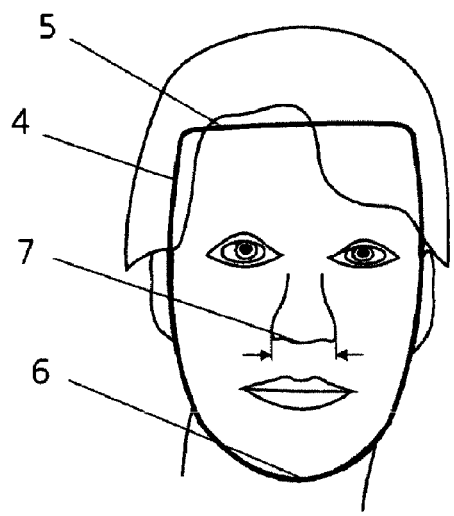
FIG. 1 shows a frontal view of the face of a patient in a line illustration.

In accordance with FIG. 1, the contours 4 of the face of the patient are determined. In this case the forehead of the patient, to be precise a transition 5 between the forehead and the cranial arch adjoining the latter, represents the top side of the front tooth 1 with the cutting edge. The chin 6 represents the dental neck.

The width of the nasal base 7 of the patient is determined in order to determine the overall width of the front teeth 1, the lateral incisors 2 and the canine teeth 3. However, this is not effected on the basis of the image record, but directly on the face of the patient in order to obtain the original width. The original width of the nasal base 7 corresponds to the overall width of the six teeth, from canine tooth tip to canine tooth tip. Using this determined overall width and knowing the individual widths of the teeth with respect to one another, it is then possible to reconstruct the width of each tooth in combination with the subsequent determinations.

Figure 2:
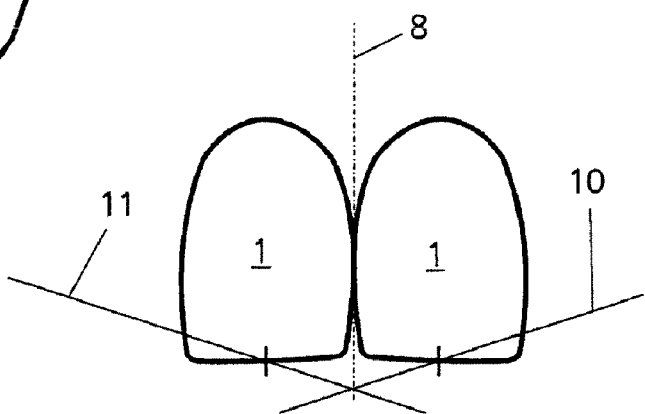
FIG. 2 shows two front teeth of the patient from the upper jaw.

In accordance with FIG. 2, the shape obtained from the facial contours in FIG. 1 is rotated through 180° for the two front teeth 1 of the upper jaw, so that the cutting edge points downward. The shape of the one front tooth obtained can be copied in a simple manner by mirroring in a vertical line 8. Thus, a reconstruction of the second front tooth 1 is also obtained.

The reconstruction of the two lateral incisors 2 becomes clear from FIGS. 2 to 6.

Figure 3:
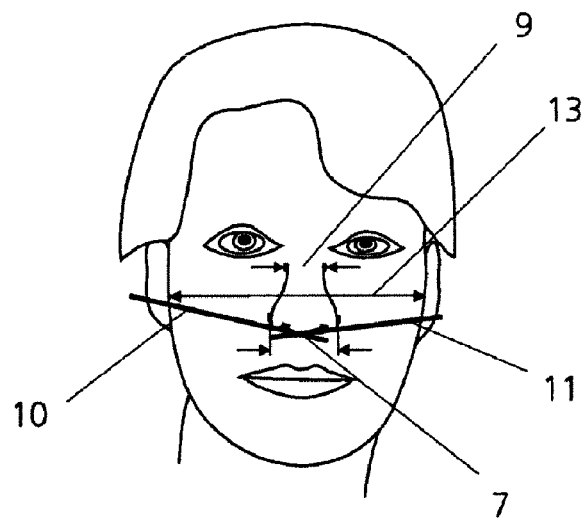
FIG. 3 shows a further illustration of the face of the patient in accordance with FIG. 1.
Figure 4:
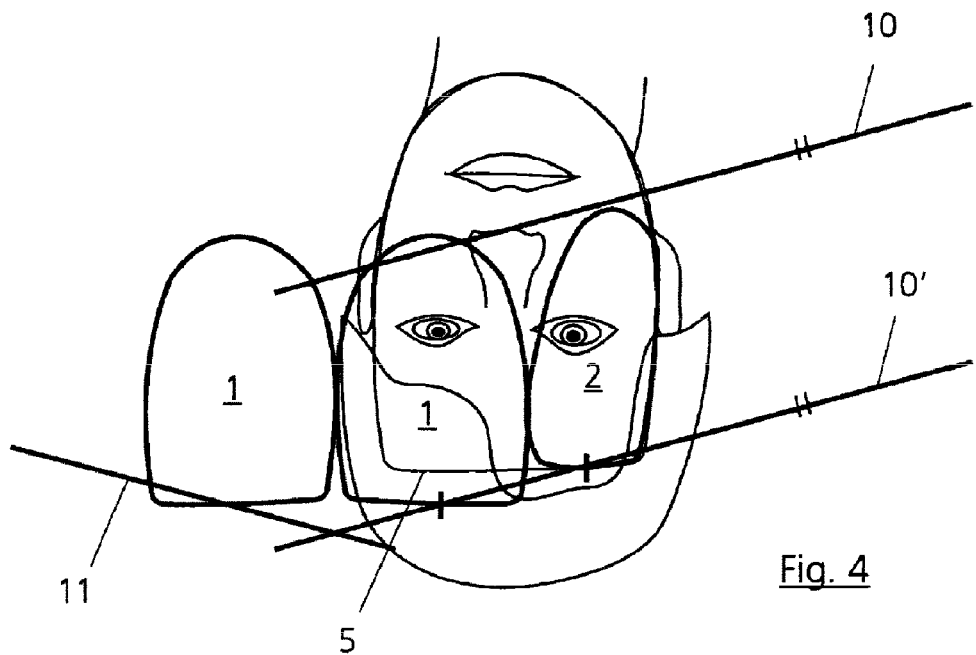
FIG. 4 shows the face of the patient with a reconstruction of one of the two lateral incisors.
Figure 7:
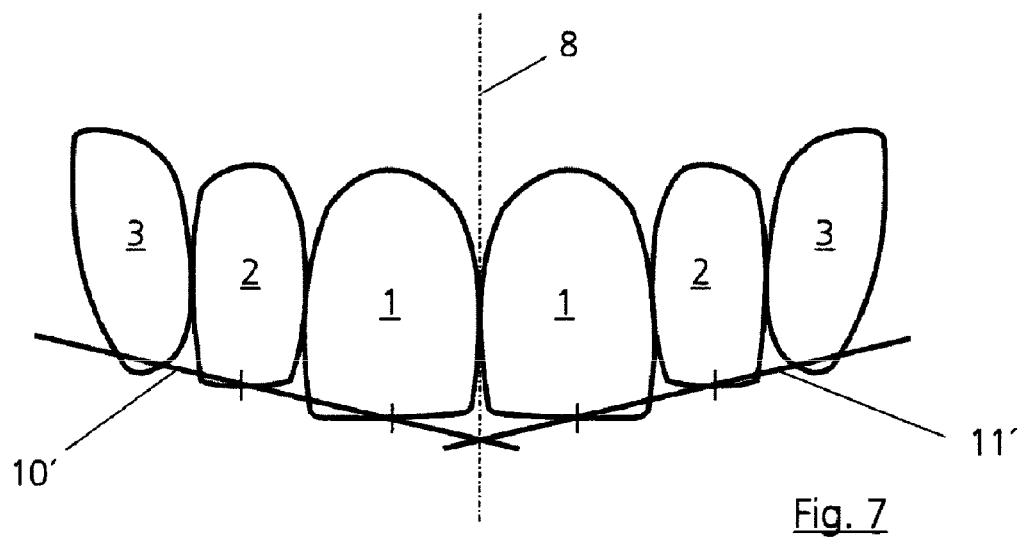
FIG. 7 shows a view of the upper jaw with the front teeth, the two incisors, and the two canine teeth.

In accordance with FIG. 3, the width of the nasal base 7 and the width of the nasal root 9 are measured on the basis of the image record (in this case the line drawing). At the same time, two diagonals 10 and 11 which define the lower end of the nose—the profile from the center of the nose via the two lateral nasal wings to be precise—are generated. The obtained and correspondingly lengthened diagonals 10 and 11 reproduce the profile of the cutting edges 12 of the front teeth 1, the incisors 2, and the canine teeth 3. The transfer of the two diagonals 10 and 11 for the purposes of reconstructing these cutting edges is clear in particular from FIGS. 5 and 7. It was found that, for a more detailed and hence more precise transfer, it was more expedient if the image used to this end was larger than, preferably double the size of, the previously depicted photographic image used for the measurements. The diagonals 10' and 11' in this case pass through the intersections of the respective central lines of the teeth at the cutting edges.

The width of the incisor 2 is reconstructed in the following way: the value of the width of the nasal base 7 obtained from FIG. 3 is divided by the value of the width of the nasal root 9. At the same time, the overall width of the face, corresponding to line 13, is determined in FIG. 3. The ratio of the result of the division (nasal base)/(nasal root) is used as divisor for the value of the overall width of the face in accordance with the image. The result obtained in this manner corresponds to the width of the incisor 2 to be reconstructed in relation to the front tooth 1.

Example: the width of the nasal base in accordance with the photo is 20.5 mm, the width of the nasal root is 14 mm, and the overall width of the face in accordance with the photo is 52 mm.

Nasal base (20.5)/Nasal root (14)=1.46

Overall width of face (52)/1.46=35.6

This means that the ratio of widths of the front tooth 1 to the incisor 2 is 52:35.6.

The outer shape of the incisor 2 is fixed by the contour of the face from the second image (on the same side). The inner shape of the incisor 2 is matched freely.

Figure 5:
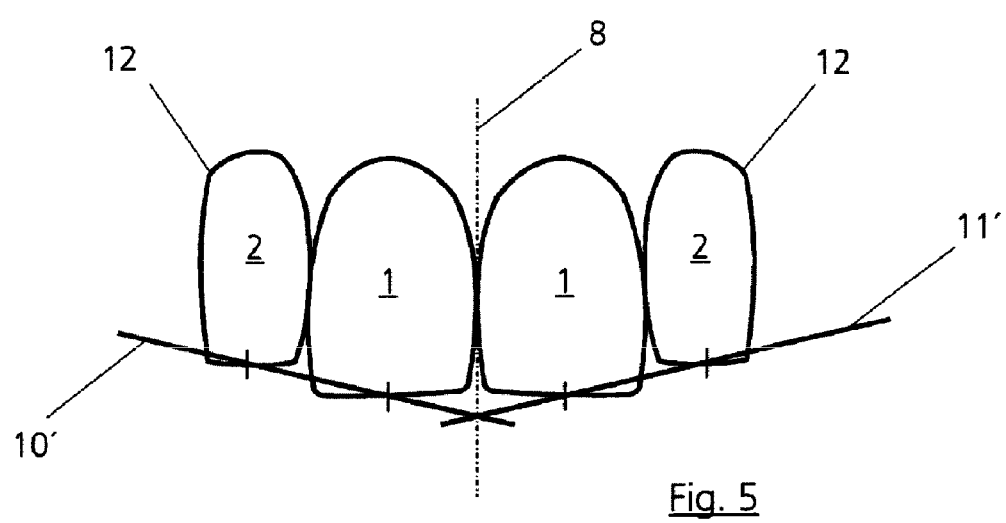
FIG. 5 shows a view of the two front teeth and the two lateral incisors.

FIG. 5 shows the frontal view of the two front teeth 1 with the two incisors 2, mirroring being undertaken—if necessary—for copying in the vertical line 8.

Figure 6:
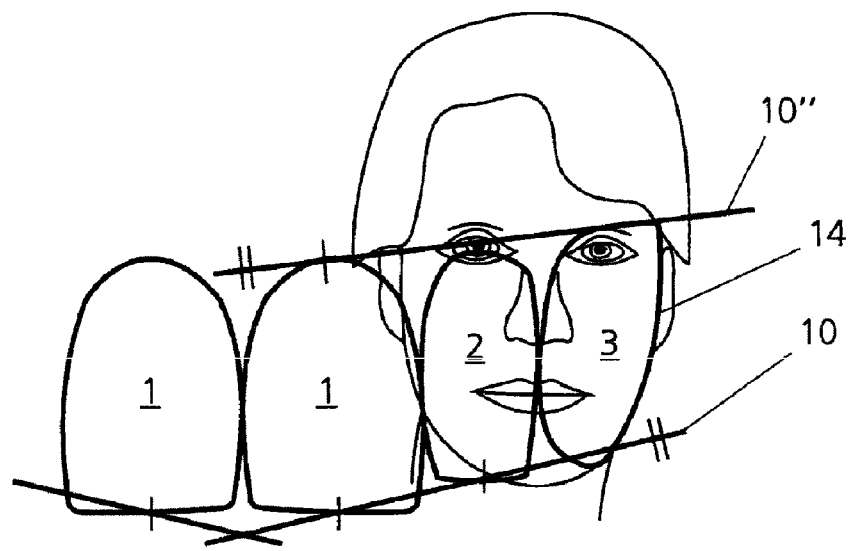
FIG. 6 shows the face of the patient with a reconstruction of a canine tooth.

FIG. 6 clarifies the reconstruction of a canine tooth 3. The outer shape 14 of the canine tooth 3 respectively facing the outside of the face corresponds to the profile of the shape of the left cheek in the case of the left canine tooth. Similarly, the profile of the outer shape of the right canine tooth corresponds to the profile of the shape of the right cheek, provided that the right canine tooth is not reconstructed in the vertical line 8 by mirroring the left canine tooth (see FIG. 7).

The height or length of the canine tooth 3 is determined in the following manner: the diagonal 10 is displaced in a parallel fashion and applied as tangent 10'' to the central line of the front tooth 1 at the intersection with the cutting edge. Subsequently, the image record is "displaced" such that the tangent 10'' passes through the right eyebrow at the right canine tooth 3.

In practice it was found that, compared to the illustrations in accordance with FIGS. 1 and 3 used for the reconstruction, larger illustrations or images are advantageous for the profile of the outer shape 14 of the canine tooth 3, just like the profile of the cutting edge 12, in order to obtain higher accuracy of details.

Since the width of a canine tooth 3 is in general 80% of the width of an incisor 2 in a frontal view, it is also possible to reconstruct the width of the canine tooth 3.

Since, in general, every human has a "strong" and a "weak" side, which is also mirrored in the human's set of teeth, this fact should also be taken into account during a reconstruction.

Figure 8:
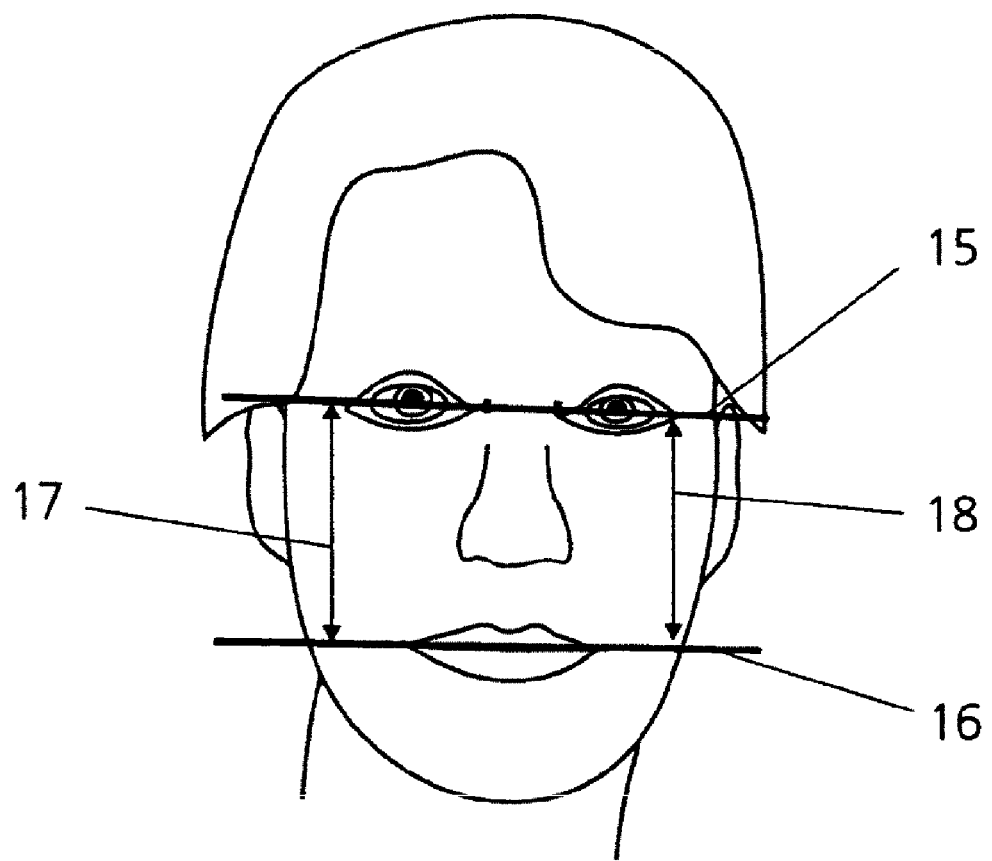
FIG. 8 shows the face of the patient with the line passing through the center of both pupils and the line passing through the corners of the mouth.

FIG. 8 clarifies the determination of the more strongly set-up side of the patient. To this end, a so-called bipupil line 15 is drawn between the two eyes and a corner of the mouth line 16 is drawn through the closed mouth of the patient. The two lines, that is to say the bipupil line 15 and the corner of the mouth line 16 are generally not precisely horizontal or parallel to one another. If the distances 17 and 18 on both sides of the nose are measured in the outer region of the face, it will be determined that in general one distance line is longer than the other. In the illustrated exemplary embodiment, the distance line 17 is slightly longer than the distance line 18. This means, since it is the right-hand side of the patient in this case and hence the right-hand side of the dentures should be set-up more strongly.

Knowing these circumstances makes it possible to fix the right-hand side of the dentures as the harmonic side.

I claim:

1. A method for reconstructing missing, broken and/or abraded teeth by means of facial analysis to determine the shapes and sizes of the teeth in relation to the face of a patient for whom the teeth are provided, the method comprising the steps of:

measuring an original width of the nasal base on the face;

ascertaining a spacing between the tips of the two canine teeth of the patient from one another according to the original width of the nasal base;

determining the proportional widths of a plurality of teeth from the ascertained spacing between the tips of the two canine teeth of the patient;

taking one or more image records of the face;

rotating the at least one image record through 180° so that the forehead is pointing downward to determine from the forehead the cutting edge of a front tooth;

determining the shape and size of at least one central front tooth by measuring the contours of the image record of the face from the forehead to the chin via the cheek;

reconstructing a second central front tooth from the first front tooth mirrored in a vertical line;

determining a width of the nasal base and a width of a nasal root by means of the image record;

dividing the width of the nasal base by the width of the nasal root;

determining a value of the overall facial width of the image record;

dividing the value of the overall facial width of the image record by the ratio obtained by the division of the width of the nasal base by the width of the nasal root; and reconstructing a width of at least one of two lateral incisors from the division of the value of the overall facial width of the image record by the ratio obtained by the division of the width of the nasal base by the width of the nasal root.

2. The method as claimed in claim 1 further comprising the step of determining the cutting edge of a front tooth by a transition from the forehead to the cranial arch.

3. The method as claimed in claim 2 further comprising the steps of:

determining two diagonals which extend laterally from the center of the nose and define the lower end of the nose;

translating the two diagonals in a parallel fashion onto the forehead of the image record; and determining the profile of the cutting edge and the height of the at least one of two lateral incisors.

4. The method as claimed in claim 3 further comprising the steps of:

producing a second image record that is at least approximately double the size of the first record;

translating the two diagonals from the first record onto the second image record;

determining the tooth profile and the outer shape of the at least one of two lateral incisors; and wherein the outer shape of the at least one of two lateral incisors is fixed by the same side contour of the face of the second record.

5. The method as claimed in claim 4 further comprising the step of determining the second of the at least one of two lateral incisors by mirroring the first of the at least one of two lateral incisors in a perpendicular line.

6. The method as claimed in claim 5 further comprising the step of determining the width of the at least one of two canine teeth from the value of 80% of the value of the width of the at least one of two lateral incisors in a frontal view.

7. The method as claimed in claim 6 further comprising the steps of:

determining the profile of the cheek located on the same half of the face as at least one of two canine teeth; and reconstructing the lateral outer shape of the at least one of two canine teeth from the profile of the cheek.

8. The method as claimed in claim 7 further comprising the steps of:

determining a tangent from the central line of the front tooth at the intersection with the cutting edge;

translating the tangent from the second image record onto the first record;

displacing the tangent such that the tangent passes through the right eyebrow located on the same side as the at least one of two canine teeth; and reconstructing the upward boundary which determines the height of the at least one of two canine teeth being affected by the eyebrow located on the same side.

9. The method as claimed in claim 8 further comprising the steps of:

determining the second of the at least one of two canine teeth by mirroring the first of the at least one of two canine teeth in a vertical line.

10. The method as claimed in one of claim 9 further comprising the steps of:

determining the distance between the bipupil line and the corner of the mouth line on each of the right side and left side of the face;

determining the harmonic side of the face from greater value of the distance between the bipupil line and the corner of the mouth line of either the right side or left side; and;

reconstructing the harmonic side of the patient as the more strongly set-up side.

\* \* \* \* \*